(12) United States Patent
Lin et al.

(10) Patent No.: US 10,561,993 B2
(45) Date of Patent: Feb. 18, 2020

(54) BUBBLE-GENERATION APPARATUS AND SYSTEM

(71) Applicants: Kechuang Lin, Xiamen (CN); Yi-Jui Huang, Xiamen (CN)

(72) Inventors: Kechuang Lin, Xiamen (CN); Yi-Jui Huang, Xiamen (CN)

( * ) Notice: Subject to any disclaimer, the term of this patent is extended or adjusted under 35 U.S.C. 154(b) by 235 days.

(21) Appl. No.: 15/607,582

(22) Filed: May 29, 2017

(65) Prior Publication Data

US 2017/0259218 A1 Sep. 14, 2017

Related U.S. Application Data

(63) Continuation of application No. PCT/CN2015/082901, filed on Jun. 30, 2015.

(51) Int. Cl.
*B01F 3/04* (2006.01)
*A61C 17/022* (2006.01)
*A61C 17/02* (2006.01)
*B01F 13/00* (2006.01)
*B01F 5/06* (2006.01)
*C02F 1/00* (2006.01)

(52) U.S. Cl.
CPC ........ *B01F 3/04113* (2013.01); *A61C 17/022* (2013.01); *A61C 17/0202* (2013.01); *A61C 17/0217* (2013.01); *B01F 3/04099* (2013.01); *B01F 3/04269* (2013.01); *B01F 5/06* (2013.01); *B01F 13/002* (2013.01); *C02F 1/00* (2013.01); *B01F 3/04* (2013.01); *B01F 3/04106* (2013.01); *B01F 2003/04404* (2013.01); *B01F 2003/04858* (2013.01)

(58) Field of Classification Search
CPC ............ A61C 17/0202; A61C 17/0217; A61C 17/022; B01F 3/04113; B01F 3/04099; B01F 3/04269; B01F 3/04; B01F 3/04106; B01F 5/06; B01F 13/002; B01F 2003/04404; B01F 2003/04858; C02F 1/00
USPC .............................. 261/81, 100, 105, 119.1
See application file for complete search history.

(56) References Cited

U.S. PATENT DOCUMENTS

| | | | | |
|---|---|---|---|---|
| 3,063,952 A | * | 11/1962 | Vieli | B29B 7/7419 261/122.1 |
| 4,793,714 A | * | 12/1988 | Gruber | B01F 3/04978 261/122.1 |
| 5,836,683 A | * | 11/1998 | Moon | B01F 11/0077 366/124 |
| 6,039,309 A | * | 3/2000 | Kuklinski | B01F 3/04241 261/1 |
| 6,572,084 B1 | * | 6/2003 | Ivanovich | B01F 3/04446 261/122.1 |

(Continued)

*Primary Examiner* — Charles S Bushey
(74) *Attorney, Agent, or Firm* — Syncoda LLC; Feng Ma

(57) ABSTRACT

A super-fine bubble generation apparatus includes a fine-array porous membrane and a device for generating substantially uniform, super-fine gas bubbles in a liquid. The fine-array porous membrane includes a plurality of pores having a substantially uniform size of <100 μm, with a variation of <20%. The super-fine gas bubbles generated by this apparatus can have a size of 50 nm-50000 nm, with a substantially uniform distribution with variations <20%. Applications of such super-fine bubble generation apparatus can include a skin cleansing device, or a teeth-cleaning device.

16 Claims, 5 Drawing Sheets

(56) References Cited

U.S. PATENT DOCUMENTS

| | | | | |
|---|---|---|---|---|
| 7,591,452 B2* | 9/2009 | Kohama | ............. | B01F 3/04262 |
| | | | | 261/102 |
| 8,181,941 B2* | 5/2012 | Von Wimmersperg | ...................... | |
| | | | | C01B 3/0015 |
| | | | | 261/105 |
| 8,302,941 B2* | 11/2012 | Nakashima | .......... | A01K 63/042 |
| | | | | 261/105 |
| 9,764,254 B2* | 9/2017 | Kobayashi | ......... | B01D 19/0031 |
| 2012/0299206 A1* | 11/2012 | Kwon | ................. | B01F 3/04269 |
| | | | | 261/29 |
| 2013/0056076 A1* | 3/2013 | Longman | ............ | B01F 3/04262 |
| | | | | 137/1 |
| 2013/0071702 A1* | 3/2013 | Longman | ............ | B01F 3/04262 |
| | | | | 429/50 |
| 2015/0272089 A1* | 10/2015 | Yu | ........................ | A01K 63/042 |
| | | | | 366/150.1 |

* cited by examiner

BUBBLE-GENERATION APPARATUS AND SYSTEM

CROSS-REFERENCE TO RELATED APPLICATIONS

The present application is a continuation of, and claims priority to, PCT/CN2015/082901, filed on Jun. 30, 2015, the disclosure of which is hereby incorporated by reference in its entirety.

BACKGROUND

Air bubbles or gas bubbles can be generated in a number of ways in a liquid such as water. For example, boiling water or cavitation can generate large air bubbles. The technology of controlling the generation and/or collapsing of gas bubbles in a liquid has been widely applied in various fields such as sewage treatment (by providing substantial mass transfer of oxygen to wastewater), industrial cleaning (by generating controlled acoustic cavitation in the cleaning fluid for cleaning contaminants), industrial mixing (by breaking down and homogenizing suspended particles in a liquid solution), and biomedical engineering (for example, to destruct kidney stones in shock wave lithotripsy).

SUMMARY

The present disclosure relates to a super-fine bubble generation apparatus or system that comprises a fine-array porous membrane, and to its practical applications.

It may be possible to generate gas bubbles using foam materials. Existing foam materials may have pore sizes of 0.5~8 mm, and may have a specific surface area of 14 3100/mm. However, the pore sizes of these foam materials have a large variation, for example >100%.

Some embodiments disclosed herein comprise high surface-area-to-volume ratio fine-array porous material. The fine-array porous material can be a fine-array membrane, having a thickness of 10 µm-50000 µm, and preferably of 100 µm-1000 µm. The fine-array porous material can have a surface area larger than 100 cm$^2$, such as 20 cm×20 cm. The sizes of the pores can be, for example, less than about 100 µm, and preferably less than about 25 µm. Compared with existing foam materials, the size of the pores in the fine-array porous material disclosed herein is substantially uniform with a variation of less than about 20% and preferably of less than about 10%. In some embodiments, the fine-array porous material can include a plurality of grain boundary regions filled with a solid material or film to increase the mechanical strength of the fine-array porous material, wherein the specific surface area is higher than 410/mm, the size variation is less than about 10%, and the grain boundary regions have a size of about 5 µm-15 cm. In some embodiments, the fine-array porous material may have little or no grain boundaries.

An apparatus for generating fine gas bubbles, and more specifically, for generating substantially uniform, super-fine gas bubbles in a liquid is disclosed herein. The apparatus may include a fine-array porous membrane with a specific surface area higher than about 410/mm, the specific surface area depending on different pore sizes. The fine-array porous membrane comprises a plurality of pores, wherein the plurality of pores have a size of less than about 100 µm, and preferably less than about 25 µm. The size of the plurality of pores is substantially uniform with a variation of less than about 20% and preferably of less than about 10%. In some embodiments, the fine-array porous membrane in the apparatus may be made of polymer, ceramic, metal, or a composite material. For examples, the fine-array porous membrane in the apparatus may be made of $SiO_2$, $TiO_2$, $Al_2O_3$, or ZnO.

The super-fine bubble generation apparatus disclosed herein also comprises a device configured to generate super-fine gas bubbles in the liquid. The device for generating super-fine gas bubbles is configured to push gas bubbles contained in the liquid on a first side of the fine-array porous membrane through to a second side of the fine-array porous membrane to generate super-fine gas bubbles in the liquid on the second side of the fine-array porous membrane.

In some embodiments, the device for generating super-fine gas bubbles comprises a high-pressure liquid injection device, configured to apply a pressure on the liquid from the first side of the fine-array porous membrane through to the second side of the fine-array porous membrane to generate super-fine gas bubbles. The liquid on the first side of the fine-array porous membrane can contain a large amount of large gas bubbles with sizes of >50 µm. The volumetric ratio between liquid and gas bubbles can be, for example, 1:1-10000:1, and preferentially 20:1-500:1.

In some embodiments, the device for generating super-fine gas bubbles comprises an ultrasound vibration device, wherein the ultrasound vibration device is disposed on the first side of the fine-array porous membrane and at a position that directionally points at the fine-array porous membrane. The ultrasound vibration device is configured to work at a frequency of >20 KHz, preferably at a range of 80 KHz-200 KHz, and at a power of <0.5 W/cm$^2$, preferably at a range of 0.01 W/cm$^2$-0.1 W/cm$^2$.

The large air bubbles at the first side of the fine-array porous membrane traverse the membrane as a result of the water pressure and/or the vibration from the ultrasound, and generate substantially uniform super-fine bubbles at the second side of the fine-array porous membrane. The size of the super-fine bubbles can be controlled by selecting the fine-array porous membrane with desired pore sizes.

In some embodiments, the liquid can be water. In some embodiments, the liquid can be an organic solvent, such as EtOH (alcohol), ACE (acetone), IPA (isopropyl alcohol), and toluene. In some embodiments, the liquid can be an oil. In some embodiments, the gas bubbles can be air bubbles, and in other embodiments, the gas bubbles can be made of a gas such as $CO_2$, $N_2$, or an inactive gas.

In some embodiments, the fine-array porous membrane can be surface-treated to improve the efficiency to generate super-fine gas bubbles, depending on the composition of the fine-array porous membrane and the type of the liquid that is used. In some embodiments where super-fine gas bubbles need to be generated in a liquid with a high viscosity, for example, oil, the fine-array porous membrane can be surface-treated to become hydrophobic or oleophylic, in order to facilitate the flow of gas bubbles through the fine-array porous membrane by reducing the electrostatic adherence of the liquid on the surface of the fine-array porous membrane. In embodiments where the fine-array porous membrane is made of a metal, such as Al, Ti, Ni and Cu, a ceramic such as $TiO_2$, $Al_2O_3$ and ZnO, or a polymer such as polystyrene and silicone, a hydrophobic group can be added to the surface of the fine-array porous membrane through dehydrolysis between the hydroxyl group of the fine-array porous membrane and the hydrophilic group of a surfactant that also contains the hydrophobic group. In one example, a fine-array porous membrane made of Cu (containing CuO or $Cu_2O$ on the surface) can be surface-treated with perfluorooctyltriethoxysilane to make the surface of the porous membrane hydrophobic. In some embodiments where a liquid with a low viscosity, such as water, is used, the fine-array porous membrane can be surface-treated to become hydrophilic, and the electric potential of the surface of the fine-array porous membrane is configured to equal to the electric potential of the gas bubbles, in order to facilitate the flow-through of the gas bubbles mediated by electro-osmosis between the liquid and the fine-array porous membrane.

DETAILED DESCRIPTION

Embodiments disclosed herein provide an apparatus or system configured to generate super-fine air bubbles, such as bubbles <50 μm in size, for example <10 μm in diameter. The size of super-fine air bubbles depends on the pore size, and is estimated to be around pore size±20%. For example, an apparatus with a pore size of 50 μm can generate super-fine air bubbles with a size of about 40-60 μm. These super-fine air bubbles can float slowly in the water. Some of the super-fine air bubbles can dissolve in the water, thereby increasing the levels of dissolved oxygen in the water. The bubbles can also burst quickly, and when a large number of bubbles burst, a lot of heat can be generated in the process. In some cases, rupture of the air bubbles can also generate ultrasonic wave and/or negative ions, etc. in the water.

The dissolved oxygen carried by the super-fine air bubbles, and the heat, ultrasonic waves, and/or negative ions generated by rupture of the super-fine bubbles can have a variety of health benefits, and thus the super-fine bubbles can be used in cosmetics or health care. As an example, super-fine bubbles with a diameter of <10 μm can easily penetrate into pores on the skin, and thus in some embodiments, the super-fine air bubble generated by the disclosed apparatus can be used in a skin cleanser product to deep clean dirt, oil and makeup from skin pores, preventing the formation of and alleviating the symptoms of acne. In another example, rupture of super-fine bubbles in water can generate a large amount of heat, ultrasonic waves and/or oxygen anions which may have therapeutic effect, and thus in some other embodiments, super-fine bubbles generated by the disclosed apparatus can be used in therapeutic products for skin care, skin cleansing, whitening, hydrating the skin, improving elasticity, alleviating athlete's foot, acne treatment and eczema treatment.

Figure 1:
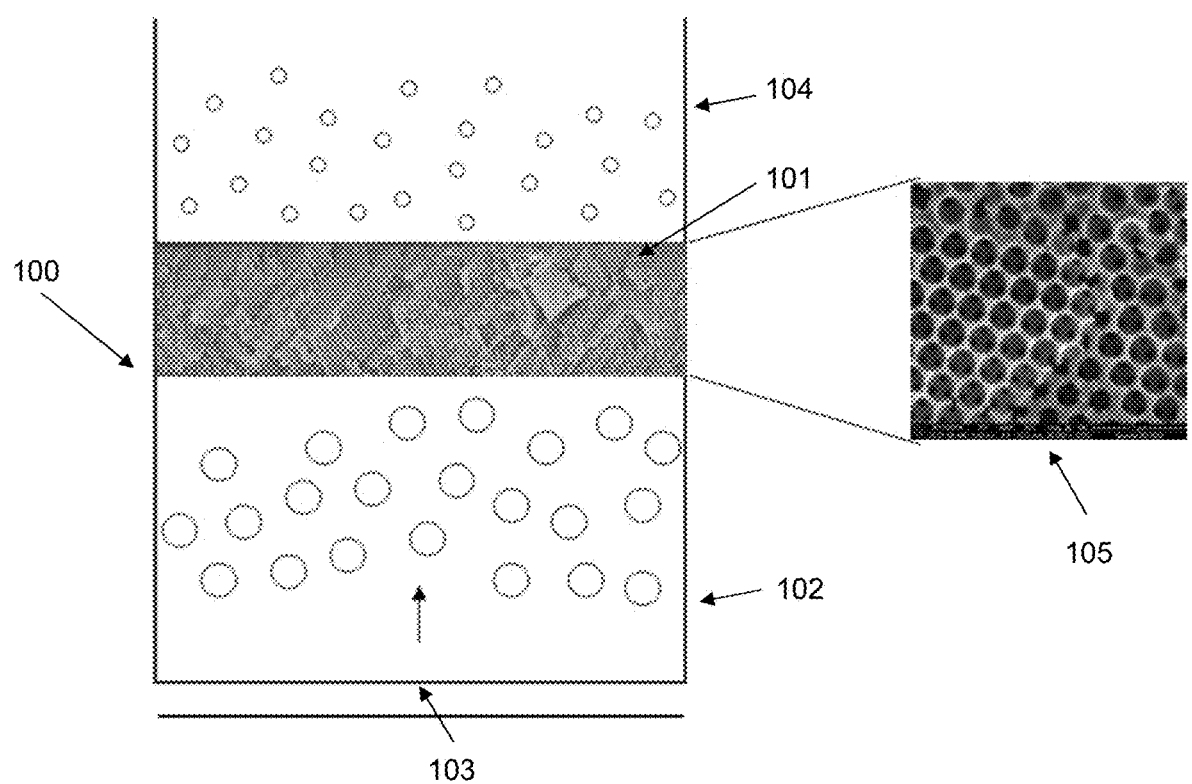
FIG. 1 illustrates a fine-bubble generation apparatus.

FIG. 1 illustrates a fine-bubble generation apparatus. The apparatus 100 comprises a fine-array porous membrane 101, a first chamber 102 filled with a large gas bubble-containing liquid on a first side of the fine-array porous membrane 101, a device for generating super-fine gas bubbles 103 disposed on one end of the first chamber 102, and a second chamber 104 containing the liquid with super-fine bubbles. A magnified view of the fine-array porous membrane is shown in 105. The fine-array porous membrane may have a thickness of 10 μm-50000 μm, and preferably of 100 μm-1000 μm. The fine-array porous membrane may have a surface area of larger than 100 cm$^2$, such as 20 cm×20 cm. The sizes of the pores can be, for example, less than about 100 μm, and preferably less than about 25 μm. The size of the pores is substantially uniform with a variation of less than about 20% and preferably of less than about 10%. Different sizes of the pores in the fine-array porous membrane can be selected to control the sizes of the super-fine air bubbles that are generated, such as 50 nm-50000 nm.

Figure 2:
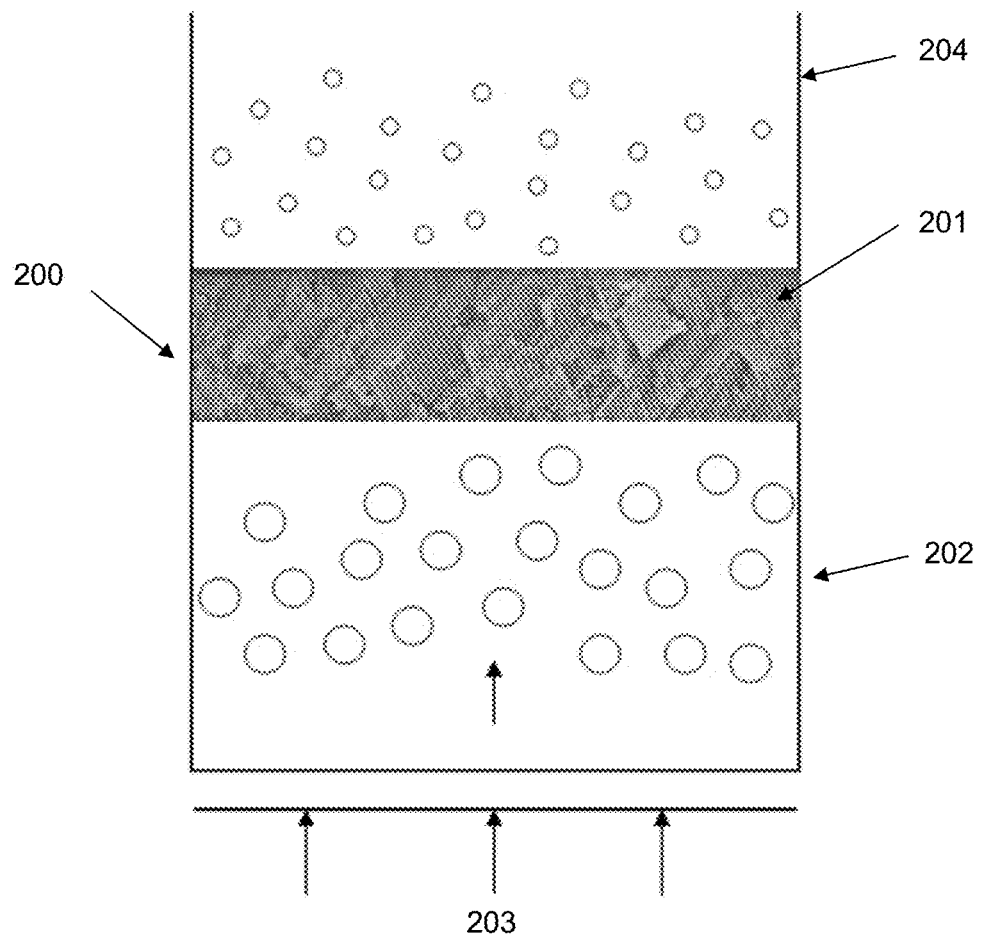
FIG. 2 illustrates a fine-bubble generation apparatus comprising a high-pressure liquid injection device according to some embodiments.

FIG. 2 illustrates a fine-bubble generation apparatus comprising a high-pressure liquid injection device according to some embodiments. In the apparatus 200, a high-pressure liquid injection device 203 is the device for generating super-fine gas bubbles, which substantially pushes the large gas bubble-containing liquid in the first chamber 202 through the fine-array porous membrane 201 to generate super-fine gas bubbles in the second chamber 204. In some embodiments, the liquid can be water and the gas bubbles can be air bubbles. In these embodiments, the high-pressure water injection device can work at a pressure of <100 Pa, and preferably of 0.1 Pa-10 Pa. Water under the high pressure can contain a large number of large air bubbles, for example with sizes of >50 μm. The volumetric ratio between water and air bubbles can be 1:1-10000:1, and preferably around 20:1-500:1. In some embodiments, other liquid, such as an organic solvent and oil, can be used. Examples of an organic solvent include EtOH (Alcohol), ACE (Acetone), IPA (isopropyl alcohol), and toluene. The pressure needs be selected based on the type of the liquid used. Overly high pressure may cause the fine-array porous membrane to break.

Figure 3:
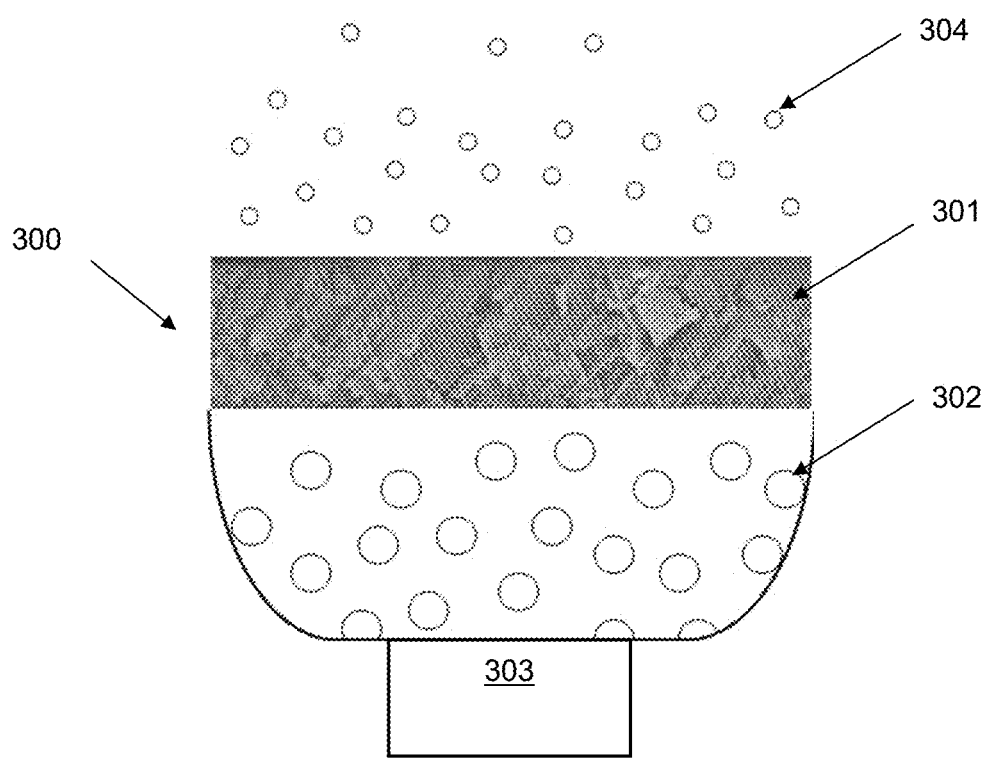
FIG. 3 illustrates a fine-bubble generation apparatus comprising an ultrasound vibration device.

In some embodiments, an ultrasound vibration device can be included in a super-fine bubble generation apparatus. As illustrated in FIG. 3, an ultrasound vibration device 303 is disposed on one end of a first chamber 302 filled with a liquid containing large gas bubbles, at a position that directionally points at the fine-array porous membrane 301, substantially allowing the ultrasonic wave released from the ultrasound vibration device 303 to push the gas bubbles in the first chamber 302 through the fine-array porous membrane 301 to generate super-fine gas bubbles in the liquid contained in a second chamber 304. The ultrasound vibration device can be configured to work at a frequency of >20 KHz, preferably at a range of 80 KHz-200 KHz, and at a power of <0.5 W/cm$^2$, preferably at a range of 0.1 W/cm$^2$-0.01 W/cm$^2$.

In both the embodiments that comprise a high-pressure liquid injection device, and the embodiments that comprises an ultrasound vibration device, the large gas bubbles at the first side of the fine-array porous membrane traverse the fine-array porous membrane under the water pressure and/or as a result of the vibration from the ultrasound, and generate substantially uniform super-fine air bubbles at the second side of the fine-array porous membrane. For example, the super-fine bubbles generated at the second side of the fine-array porous membrane can have a diameter distribution within about ±20%. The size of the bubbles can be controlled by selecting the film with desired pore sizes.

In some embodiments, the fine-array porous membrane can be surface treated to become hydrophilic or hydrophobic, depending on the type and nature of the liquid that is used. In some embodiments where a liquid with a high viscosity is used, the fine-array porous membrane can be surface-treated to become hydrophobic, in order to facilitate the flow of gas bubbles through the fine-array porous membrane by reducing the electrostatic adherence of the liquid on the surface of the fine-array porous membrane. In some embodiments where a liquid with a low viscosity, such as water, is used, the fine-array porous membrane can be surface-treated to become hydrophilic, and the electric potential of the surface of the fine-array porous membrane is configured to equal to the electric potential of the bubbles, in order to facilitate the flow-through of the gas bubbles via electro-osmosis between the liquid and the fine-array porous film.

Figure 4:
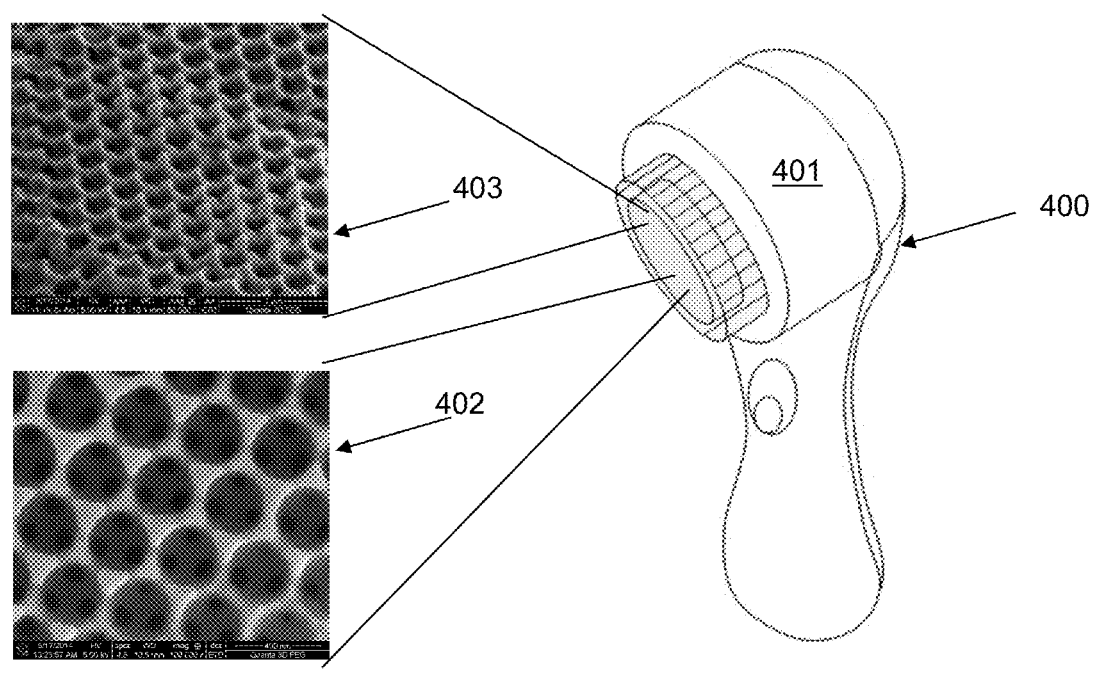
FIG. 4 illustrates a skin cleansing device having a fine-bubble generation apparatus.

FIG. 4 illustrates a skin cleansing device 400 having a fine-bubble generation device 401. The fine-bubble generation device 401 is disposed inside a head device of the skin cleansing device 400, and is configured to push a skin-cleansing liquid containing large air-bubbles outward through a fine-array porous membrane 402 to generate skin-cleansing liquid containing super-fine air bubbles in a controllable manner. A high-pressure liquid injection device or an ultrasound vibration device may be used for this purpose. The super-fine air bubbles generated by this skin care apparatus can carry an increased level of oxygen and negative ions, and can also easily penetrate into pores on the skin for deep cleaning and for cosmetic care. This skin cleansing apparatus may further comprise a plurality of brushes 403 perpendicularly disposed on the outer surface of the fine-array porous membrane 402. In some embodiments, the plurality of brushes comprise fine-array porous filaments and may have a diameter of less than about 1 μm, which can further enhance the beneficial effect brought about by the super-fine bubbles generated by the skin cleansing apparatus.

Figure 5:
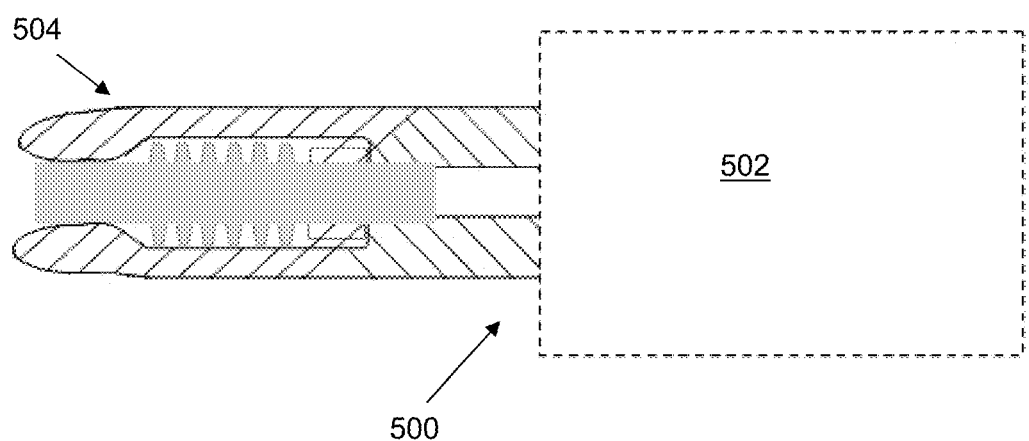
FIG. 5 is a diagram illustrating a teeth cleaning device having a fine-bubble generation apparatus.

FIG. 5 is a diagram illustrating a teeth-cleansing device 500 having a super-fine air bubble generation device 502 and a water jet head device 504. The water jet head device 504 is configured to connect with the super-fine air bubble generation device 502, such that the teeth cleansing liquid containing super-fine air bubbles generated by the super-fine air bubble generation device 502 is transferred to and accelerated by the water jet head device for dental floss. In some embodiments, the water jet head device 504 further contains a fine-array porous material similar to the brushes of FIG. 4, which can brush the teeth while flossing with the water jet.

Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. An apparatus for generating substantially uniform, super-fine gas bubbles in a liquid, comprising:
a fine-array porous membrane, and
a device configured to generate super-fine gas bubbles in a liquid, wherein:
the fine-array porous membrane comprises a plurality of pores, wherein the plurality of pores have a size of less than about 100 μm, and the size of the plurality of pores is substantially uniform with a variation of less than about 20%;
the device is configured to push gas bubbles contained in the liquid on a first side of the fine-array porous membrane through to a second side of the fine-array porous membrane to generate super-fine gas bubbles in the liquid on the second side of the fine-array porous membrane; and
wherein the fine-array porous membrane is surface-treated with perfluorooctyltriethoxysilane to be hydrophobic, and the fine-array porous membrane is made of Cu, and the fine-array porous membrane is surface-treated.

2. The apparatus of claim 1, wherein the fine-array porous membrane has a thickness of about 10 μm-50000 μm.

3. The apparatus of claim 2, wherein the fine-array porous membrane has a thickness about 100 μm-1000 μm.

4. The apparatus of claim 1, wherein the plurality of pores have a size of less than about 25 μm.

5. The apparatus of claim 1, wherein the size of the plurality of pores is substantially uniform with a variation of less than about 10%.

6. The apparatus of claim 1, wherein the device comprises a high-pressure liquid injection device, and wherein the high-pressure liquid injection device is disposed on the first side of the fine-array porous membrane.

7. The apparatus of claim 6, wherein the high-pressure liquid injection device is configured to work at a pressure of less than about 100 Pa.

8. The apparatus of claim 7, wherein the high-pressure liquid injection device is configured to work at a pressure of about 0.1 Pa-10 Pa.

9. The apparatus of claim 8, wherein the liquid at the first side of the fine-array porous membrane contains gas bubbles having a size of more than about 50 μm and have a volumetric ratio between the liquid and the gas bubbles of about 1:1-10000:1.

10. The apparatus of claim 9, wherein the gas bubbles have a volumetric ratio of about 20:1-500:1.

11. The apparatus of claim 1, wherein the device comprises an ultrasound vibration device, wherein
the ultrasound vibration device is disposed on the first side of the fine-array porous membrane and at a position that directionally points at the fine-array porous membrane.

12. The apparatus of claim 11, wherein the ultrasound vibration device is configured to function at a frequency of higher than about 20 KHz and at a power of lower than about 0.5 W/cm$^2$.

13. The apparatus of claim 12, wherein the ultrasound vibration device is configured to function at a frequency of about 80-200 KHz, and at power of about 0.1 W/cm$^2$-0.01 W/cm$^2$.

14. The apparatus according to claim 1, wherein the apparatus is configured as a skin cleansing apparatus, comprising a plurality of brushes, wherein the plurality of brushes comprises a plurality of fine-array porous filaments having a diameter of less than about 1 μm.

15. A teeth-cleaning apparatus comprising the apparatus according to claim 1, further comprising:
a water jet head device, wherein:
the water jet head device is connected to the super-fine bubble generation device such that a liquid containing super-fine air bubbles generated by the super-fine air bubble generation device is transferred to and accelerated by the water jet head device.

16. The teeth-cleaning device according to claim 15, wherein the water jet head device comprises a plurality of fine-array porous filaments having a diameter of less than about 1 μm.

\* \* \* \* \*